United States Patent [19]

Athas et al.

[11] Patent Number: 5,803,903
[45] Date of Patent: Sep. 8, 1998

[54] SURGICAL RETRACTOR AND METHOD OF USE WITH BALLOON DISSECTION

[75] Inventors: William L. Athas; William S. Eubanks, Jr., both of Durham; Thomas B. Miller, Garner, all of N.C.

[73] Assignee: MIST, Inc., Smithfield, N.C.

[21] Appl. No.: 911,609

[22] Filed: Aug. 15, 1997

[51] Int. Cl.⁶ ................................................. A61B 17/02
[52] U.S. Cl. ........................................ 600/231; 600/201
[58] Field of Search .................................. 600/201, 231, 600/232, 233

[56] References Cited

U.S. PATENT DOCUMENTS

| | | | |
|---|---|---|---|
| Re. 32,021 | 11/1985 | Scott, Jr. | 600/233 |
| 2,493,598 | 1/1950 | Rozek | 600/233 |
| 2,845,925 | 8/1958 | Jayle | 600/233 |
| 3,970,075 | 7/1976 | Sindelar et al. | 600/231 |
| 4,037,589 | 7/1977 | McReynolds | 600/232 |
| 4,274,398 | 6/1981 | Scott, Jr. | 600/233 |
| 4,813,401 | 3/1989 | Grieshaber | 600/231 |
| 4,953,540 | 9/1990 | Ray et al. | 600/233 |
| 4,971,038 | 11/1990 | Farley | 600/231 |
| 5,582,577 | 12/1996 | Lund et al. | |
| 5,651,762 | 7/1997 | Bridges | 600/201 |

*Primary Examiner*—Paul J. Hirsch
*Attorney, Agent, or Firm*—Jenkins & Wilson, P.A.

[57] ABSTRACT

A surgical retractor for use in combination with balloon dissection of internal body tissue of a human body part to maintain an operative space created by the dissection of the internal body tissue. The retractor has a frame comprising a base with opposing sides and at least one arcuate body tissue support element extending upwardly from one side to the other side of the base so as to form an arc extending transversely over a human body part wherein internal body tissue is to be balloon dissected. As least one suture anchor element is located along the length of the arcuate support element to allow a tensioning suture extending from separated internal body tissue of the human body part being balloon dissected to be secured thereto to maintain an open operation cavity. The suture tied at one end to the suture anchor element includes a disk or suture button at the other end that is urgingly retained against the top portion of the operation cavity to facilitate maintaining an open cavity for a surgical procedure.

24 Claims, 5 Drawing Sheets

SURGICAL RETRACTOR AND METHOD OF USE WITH BALLOON DISSECTION

TECHNICAL FIELD

The present invention relates generally to a surgical retractor for maintaining an operative space during surgery. More specifically, the invention relates to a retractor apparatus for maintaining balloon dissection space during surgery by supporting human body tissue defining the operative space with an external frame to which sutures extending from the operative space are secured.

BACKGROUND ART

It is well known that tissue dissection along natural tissue planes in order to create an operative space at a surgical site has recently been an active area of new medical device development. A recent development of the past decade that has achieved a degree of popularity entails dissecting human body part tissue along natural tissue planes in order to separate the layers to create a desired operating space. Representative patents directed to procedures and devices that incorporate an inflatable balloon to carry out the balloon dissection procedure include the following: U.S. Pat. No. 5,309,896; U.S. Pat. No. 5,269,753; published PCT International Application No. WO 92/212 95; published PCT International Application No. WO 93/097 22; and U.S. Pat. No. 5,607,441. Many other patents have issued that relate to balloon dissection procedures and devices, but the references set forth hereinbefore are believed to be representative.

Of course, as an alternative to balloon dissection, a surgeon can carry out the prior art manual dissection procedure that does not require the use of an inflatable balloon device. However, this procedure is believed to be deficient in many applications when compared with the balloon dissection procedure developed within the last decade.

Unfortunately, presently known balloon dissection procedures, although effective in developing an operative space during balloon dissection surgery, suffer from shortcomings related to attempting to maintain the operative space during a surgical procedure. In other words, it is difficult to maintain the operative space in an open configuration during the surgical procedure, and the operative space is many times compromised so as to result in a poor working space during a surgical procedure within the operative space. This is due to the fact that all methods presently known to applicants utilize internal structures in an effort to maintain the integrity of the optical space during surgery, and presently known internal techniques for maintaining the operative space do not provide reliable performance. The result is that the surgical procedure is made more difficult for physicians and surgical assistants due to partial or full collapsing of the operative space defined by the balloon-dissected body tissue layers.

In view of the deficiencies inherent in attempting to internally maintain a balloon-dissected operative space during a surgical procedure, the surgical community has a long-felt need for a reliable retractor for maintaining an operative space during endoscopic balloon dissection surgery. Applicants have developed a novel apparatus and procedure in order to meet the long-felt need for such a retractor apparatus for use in maintaining a balloon-dissected operative space during a surgical procedure. The device and method are described hereinbelow in order to provide a better understanding of the invention.

SUMMARY OF THE INVENTION

In accordance with the present invention, applicants provide a retractor apparatus for use with balloon dissection of internal body tissue of a human body part during a surgical procedure. The apparatus comprises a frame having a base with opposing sides and at least one arcuate body tissue support element extending upwardly from one side to the other side of the base so as to define an arc extending transversely over and in spaced-apart relationship to the human body part being balloon-dissected during surgery. At least one suture anchor element is provided at a location along the length of the arc of the body tissue support element so as to allow a retraction suture extending from the operative cavity of a human body being balloon-dissected to be secured thereto to facilitate maintaining an open cavity within the dissected internal body tissue.

The method of applicants' invention for balloon dissection of internal body tissue of a human body part during surgery by using an external retractor apparatus to maintain an open cavity within the dissected internal body tissue includes the step of providing a human body part upon which balloon dissection will be performed. Next, the human body part is positioned within the external retractor apparatus which comprises a base with opposing sides and at least one arcuate body tissue support element extending upwardly from one side to the other side of the base so as to extend transversely over and in spaced-apart relationship to the body part. Next, at least one suture is pulled from within the dissected body tissue cavity and outwardly of the human body part so that one end of the suture remains trapped within the cavity and the other end is secured under tension to a suture anchor element located along the length of the arcuate body tissue support element. In this fashion, the dissected internal body tissue of the human body part is maintained by the external retractor apparatus of the invention in an open operative space or open cavity configuration to facilitate the surgical procedure therein.

It is therefore the object of the present invention to provide a self-retaining retractor and method of use for the maintenance of an operating optical cavity.

It is another object of the present invention to provide a simple and easy-to-use external retractor framework and method of use for maintaining the operating optical cavity during endoscopic balloon-dissection surgery in order to minimize physician fatigue and optimize the success of the surgical procedure being performed within the operating optical cavity.

Some of the objects of the invention having been stated hereinabove, other objects will become evident as the description proceeds, when taken in connection with the accompanying drawings as described hereinbelow.

BEST MODE FOR CARRYING OUT THE INVENTION

Figure 1:
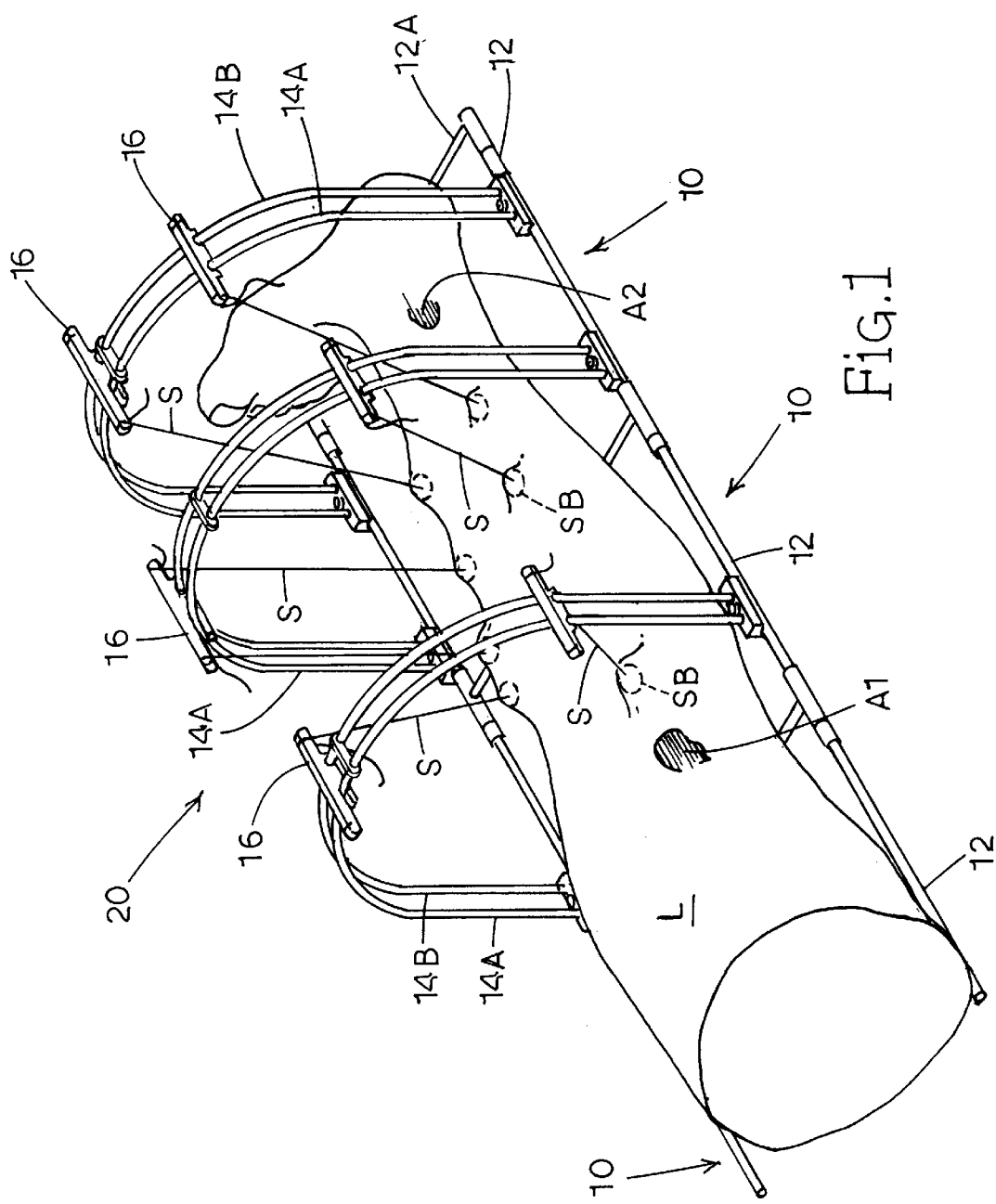
FIG. 1 is a perspective view of the surgical retractor of the present invention shown with a human leg positioned therein wherein the optical cavity created by balloon dissection is being maintained during harvesting of a saphenous vein from the leg during cardiac by-pass surgery.
Figure 2:
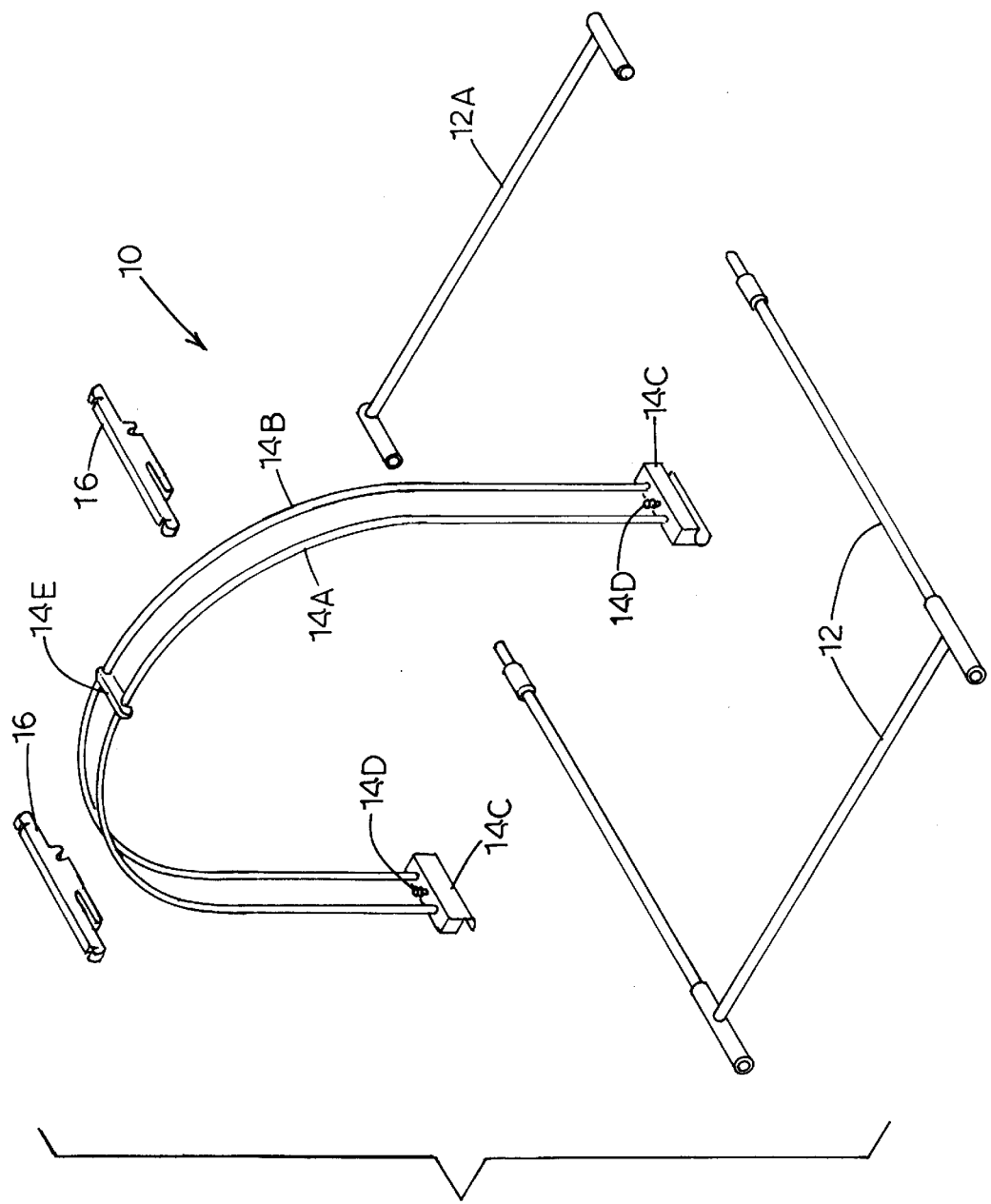
FIG. 2 is an exploded view of the surgical retractor of the present invention.
Figure 3:
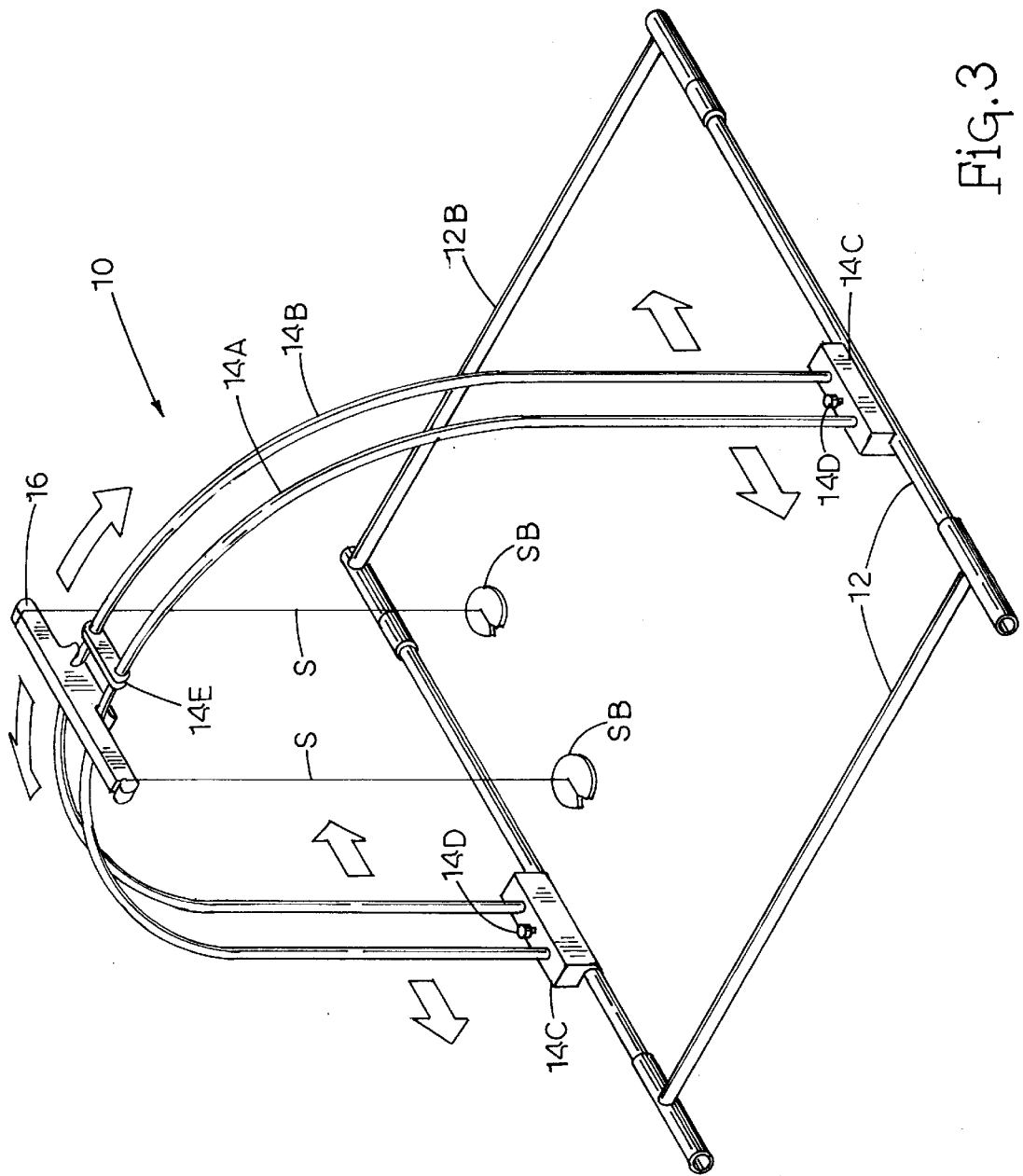
FIG. 3 is a perspective view of the surgical retractor of the present invention illustrating the adjustability of the arcuate body tissue support element and the suture anchor element.
Figure 4:
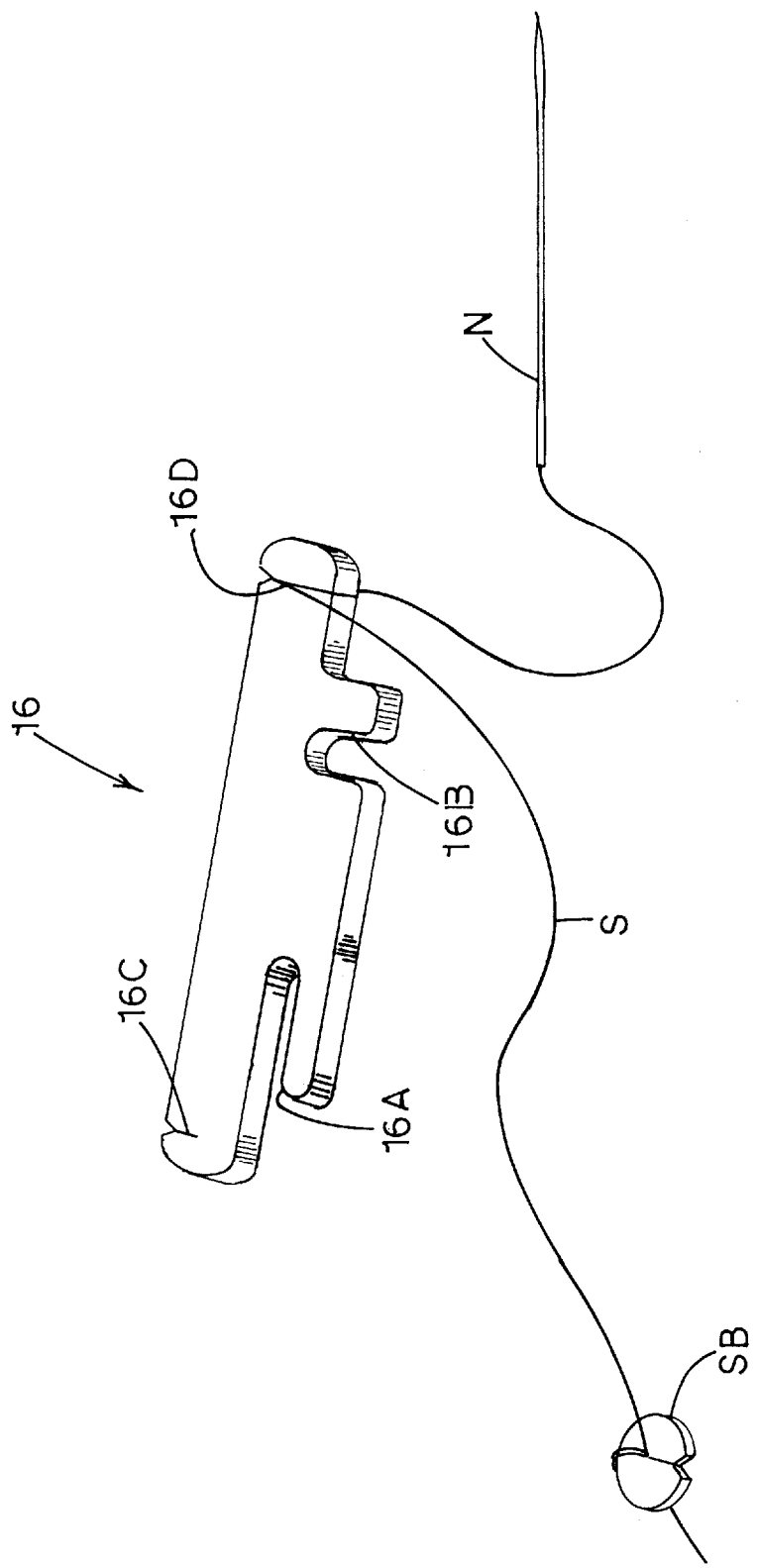
FIG. 4 is a perspective view illustrating how a suture is secured to a suture anchor element of the surgical retractor of the present invention.
Figure 5:
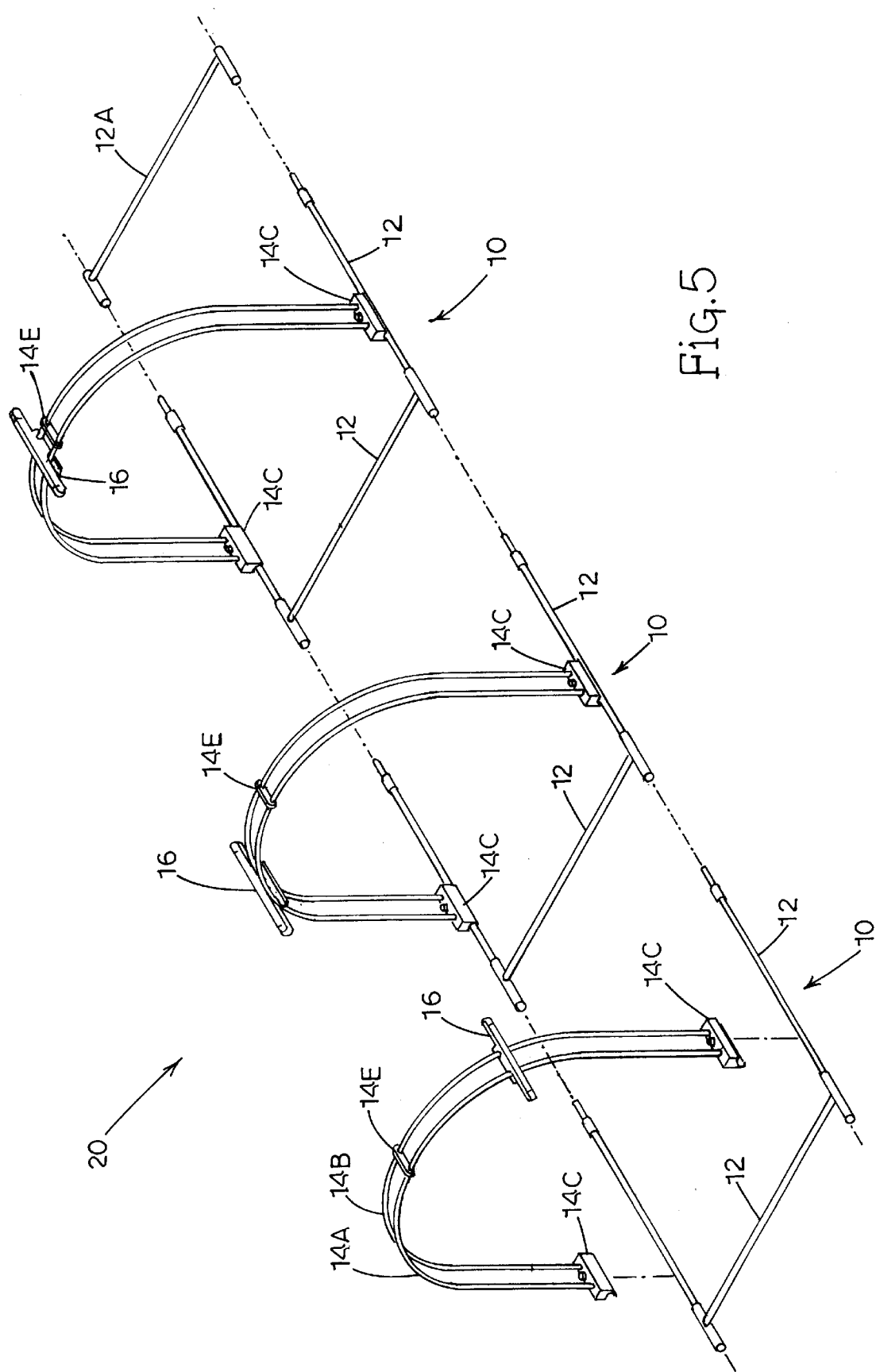
FIG. 5 is a perspective view illustrating the formation of an assembly of three retractors of the present invention into an enlarged modular embodiment for use with a leg or arm.

Referring now to FIGS. 1–5 of the drawings, the preferred surgical retractor of the present invention in shown and generally designated 10. It will be appreciated that for clarity of explanation the general designation 10 is being used to indicate a single retractor as best seen in FIGS. 2 and 3, and a modular assembly of a plurality of individual units into an extended unit as best seen in FIGS. 1 and 5 of the drawings is generally designated 20.

As will be explained in more detail hereinbelow, applicants contemplate that retractor apparatus 10 can be a single self-retaining retractor or a modular assembly 20 consisting of two or more of the self-retaining retractors assembled into an extended-length configuration. Applicants contemplate that a single retractor 10 can be use for maintaining an optical operating cavity during surgery on the head or neck (or a child's limb) whereas the extended modular retractor 20 may be required for maintaining the operating optical cavity during endoscopic balloon dissection surgery on an extended body part such as the leg or arm.

Applicants contemplate that retractor 10 can be used in combination with balloon dissection of internal body tissue to provide support to the operative space or cavity in surgical procedures on the leg, arm, head and neck. For example, retractor 10 is particularly well adapted for use during surgery on the leg to remove a saphenous vein during coronary by-pass surgery. Retractor 10 would serve to hold up the operative cavity formed by balloon dissection so as to facilitate removal of a saphenous vein by the surgeon. Also, retractor 10 could be advantageously used in the well-known procedure of securing a plate to a broken bone in the arm or leg to facilitate healing. Normally, the surgical procedure of introducing and securing the plate to the bone is complicated by difficulty in maintaining the operative cavity subsequent to balloon dissection of the internal body tissue or requires a traditional, long incision over the area designated for bone plating. However, applicants' retractor 10 can be used to facilitate maintenance of the cavity so as to enable easier introduction and securement of the plate to the arm or leg bone by a surgeon. Other potential uses (e.g., harvesting a nerve, muscle or tendon for transfer to another area of the body) of retractor 10 will be appreciated by those familiar with balloon dissection of bodily tissues to form an operative cavity during a surgical procedure.

Surgical retractor 10 can be seen from the drawings to comprise a base 12 having an end cap element 12A for removable securement thereto (see particularly FIGS. 2, 3 and 5). An arcuate support element 14 is provided to form an arch extending from one side of base 12 to the other side of base 12. Arcuate support element 14 is formed from two spaced-apart rods 14A, 14B that are secured at each end to a clamp 14C. Clamp 14C is formed so as to have an outwardly facing arcuate channel that will substantially receive a respective side of base 12 therein when support element 14 is resiliently urged together and then released to be attached to base 12. Arcuate support element 14 can be slidably adjusted along the length of the side elements of base 12 to a predetermined desired location and additional support elements 14 can be added as needed. At a desired location, a set screw 14D is provided in each clamp 14C so as to secure the clamp to the predetermined location on the side element of base 12.

As a matter of design choice, a spacer bar 14E is provided at the top of arcuate support element 14 to maintain rods 14A, 14B forming arcuate support element 14 in spaced-apart and parallel relationship. Finally, (and with particular reference to FIGS. 2, 3 and 4) one or more suture anchor elements 16 are provided that are adapted to be snapped onto arcuate support element 14 at one or more predetermined locations along the arcuate length thereof in order to provide a tie-off or securement for a suture in a manner that will be described hereinbelow. Suture anchor elements 16 (see FIG. 4) are formed with two spaced-apart slots 16A, 16B within the bottom surface thereof for removably snapping onto or engaging rods 14A, 14B of arcuate support element 14. Also, suture anchor element 16 is provided with slots 16C, 16D at opposing ends of the top surface for fixedly receiving and retaining a suture therein (typically by placing the suture into a slot and wrapping the suture around anchor element 16). Suture S, as best seen in FIG. 4, is normally attached at one end to surgical needle N and at the other end to a suture button SB (typically by wrapping) that is used to maintain a balloon-dissected operative cavity during surgery as explained in more detail hereinafter.

Although the components of surgical retractor 10 can be formed from many different types of materials as a matter of design choice, applicants' preferred embodiment of the invention utilizes stainless steel for frame 12 and either stainless steel or a translucent polymer for arcuate support element 14. Translucent polymer support elements 14 would be used to facilitate taking x-rays of a human body part positioned in retractor 10. Further, suture button SB to which one end of suture S is secured and which is used to maintain the integrity of a surgical cavity formed by balloon dissection is preferably formed from a translucent polymer or a radiopaque polymer to facilitate the taking of x-rays of a human body part positioned in retractor 10. Finally, applicants contemplate that the preferred embodiment of suture anchor element 16 is formed of a suitable plastic polymer.

FIG. 5 of the drawings illustrates a modular embodiment of a plurality of retractors 10 wherein three individual retractors 10 have been combined lengthwise to form an extended modular embodiment 20 of the retractor. The three individual retractors 10 are removably attached as indicated by the phantom lines and end cap element 12A is attached at the far end to complete the assembly of modular embodiment 20 of retractor 10. Modular embodiment 20 of retractor 10 can also be seen in use in FIG. 1 with human leg L positioned therein. As can be appreciated by one skilled in the art with reference to FIG. 1, retractor 20 is being utilized to maintain an open balloon-dissected surgical cavity with an external framework to which a plurality of sutures S are secured at one end and the other ends of sutures S are being retained within the surgical cavity by means of suture buttons SB to which the ends are attached.

As will be explained in more detail below, during a surgical procedure such as the harvesting of a saphenous vein from a patient's leg for use in cardiac by-pass surgery, a leg is entered at two remote apertures A1 and A2 (see FIG. 1) during the formation of the surgical cavity and the subsequent harvesting of the saphenous vein. To facilitate maintenance of the surgical cavity formed by balloon dissection of internal body tissue along natural tissue planes, surgical needles N are inserted into aperture A1 and/or A2, advanced into the surgical cavity (not shown) and then directed upwardly and outwardly so as to facilitate tying-off or securing sutures S trailing surgical needles N (wherein needle N will be removed after the sutures are secured to their respective anchor elements 16) on selected suture anchor elements 16 so that suture buttons SB secured to opposing ends of sutures S are under tension against the top portion of the surgical cavity. In this manner, the surgical cavity is maintained in an open position and collapse avoided so as to facilitate the surgical procedure of, for example, removal of a saphenous vein from leg L by a surgeon in conjunction with a cardiac by-pass operation.

The procedure for using applicants' retractor 10 will now be explained in detail for full clarity of understanding of applicants' novel retractor and method of use during balloon dissection in endoscopic fascial cleft surgery.

In use, retractor 10 may be utilized during balloon dissection in endoscopic fascial cleft surgery. Retractor 10, as noted above, is contemplated for use during balloon dissection of internal body tissues of the head and neck as well as the extremities such as the leg or arm.

For purposes of illustration, applicants will now describe use of retractor 10 in relationship to balloon dissection in endoscopic fascial cleft surgery on a leg. Typically, the extended modular embodiment 20 of retractor 10 will be used although the use for purposes of illustration will be described in terms of single retractor unit 10. Leg L is normally prepared and draped in a conventional sterile manner. Frame 12 of retractor 10 is then placed on an operating table underneath leg L. Arcuate tissue support elements 14 are next secured to frame 12 by placing them over the area of the leg selected for operation and securing them to frame 12. A skin incision is made on the leg and dissection proceeds to the level of the fascia. The fascia is identified and a plane developed between the deep and superficial layers of the fascia. A conventional balloon dissection device is then inserted between the deep and superficial fascia and advanced to the chosen area for the surgical procedure. The balloon is expanded so as to create a cavity between the fascial planes that will serve as the optical operating cavity throughout the operation. The balloon is then deflated and the balloon dissection device removed from leg L.

Conventional hand-held retractors are now inserted through the incision, and the skin subcutaneous tissue and superficial fascia are elevated with the hand-held retractors. The operating cavity of leg L is examined under endoscopic visualization, and a device holding a needle N with suture S and suture button SB attached thereto is advanced into the operating cavity to a point within the cavity that is selected for passage of needle N through the superficial tissue layers. Suture S is consequently advanced through the same tissue planes, and the opposite end of suture S from needle N that is attached to suture button SB will abut the tissue on the superficial aspect of the inner surface of the optical cavity. Tension is placed outside of the skin on suture S, and suture S is retracted in an upward position and attached to a selected suture anchor element 16 at one of two top slots 16C, 16D. The procedure of placing retraction sutures S into the optical cavity is repeated a multiplicity of times at various locations within the cavity in order to provide maintenance of an adequate and somewhat symmetrical operating cavity.

Alternatively, a needle N can be passed directly through the skin from outside of the body part to the inside of the operating cavity. During this procedure, needle N is pulled out through the optical cavity and through aperture A1 or A2. Suture button SB is then attached to the needle end of suture S and needle N is then removed from suture S. The other end of suture S extending from the skin of the body part is then retracted and attached to a selected suture anchor element 16 of retractor 10 so as to place suture S under tension. This process of placing the suture button SB onto a suture S is repeated a multiplicity of times to provide adequate retraction of the operating cavity.

An operation is then performed on leg L under endoscopic guidance after the operation cavity has been adequately established and retracted as best shown in FIG. 1. At the conclusion of the operation on leg L, sutures S may be cut outside of the skin of leg L. Suture buttons SB that are attached to sutures S are grasped with an endosurgical clamp under endoscopic visualization and withdrawn through initial skin aperture A1 and/or A2. Each of the retracting points is managed in an identical fashion.

Thereafter, following removal of all suture buttons SB, the initial skin incision at apertures A1, A2 is closed, and arcuate support elements 14 are removed from retractor frame 12 of retractor 10. The wounds to leg L are then bandaged in a conventional manner. In this fashion, applicants' retractor and method of use provide for a self-retaining retractor for the maintenance of an operating optical cavity during endoscopic balloon dissection surgery.

It will be understood that various details of the invention may be changed without departing from the scope of the invention. Furthermore, the foregoing description is for the purpose of illustration only, and not for the purpose of limitation—the invention being defined by the claims.

What is claimed is:

1. A retractor apparatus for use with balloon dissection of internal body tissue of a human body part, said apparatus comprising:
   (a) a frame comprising a base with opposing sides and at least one arcuate body tissue support element extending upwardly from one side to the other side of said base, said support element defining an arc extending transversely over and in spaced-apart relationship to a human body part being balloon dissected; and
   (b) at least one suture anchor element located at a location along the length of the arc of said body tissue support element to allow a tensioning suture extending from a human body part being balloon dissected to be secured thereto to maintain an open cavity within the dissected internal body tissue.

2. A retractor apparatus according to claim 1 wherein said frame comprises a plurality of said support elements that are removably attachable to selected locations along the length of the opposing sides of said base.

3. A retractor apparatus according to claim 2 wherein said support elements each comprise set screws at each end thereof for securement to the opposing sides of said base.

4. A retractor apparatus according to claim 2 including a plurality of adjustable suture anchor elements for each of said plurality of support elements.

5. A retractor apparatus according to claim 1 including a plurality of sutures each having a first end for being attached to a suture button and a second end for being secured to said at least one suture anchor element.

6. A retractor apparatus according to claim 5 wherein said suture buttons are formed from material selected from the group comprising radiopaque or translucent polymer.

7. A retractor apparatus according to claim 1 wherein said base and said support element are constructed of stainless steel.

8. A retractor apparatus according to claim 1 wherein said base is formed of stainless steel and said support element is formed of translucent polymer.

9. A retractor apparatus according to claim 1 comprising a plurality of said frames being detachably secured together to form an extended length retractor apparatus.

10. A retractor apparatus according to claim 9 wherein said plurality of frames consists of three frames.

11. A retractor apparatus for use with balloon dissection of internal body tissue of a human body part, said apparatus comprising:

(a) a frame comprising a base and with opposing sides and a plurality of arcuate body tissue support elements extending upwardly from one side to the other side of said base, said support elements defining an arc for extending transversely over and in spaced-apart relationship to a human body part being balloon dissected; and (b) a plurality of suture anchor elements adapted to be adjustably secured at selected locations along the length of the arc of each of said body tissue support elements to allow tensioning sutures extending from a human body part being balloon dissected to be secured thereto to maintain an open cavity within the dissected internal body tissue.

12. A retractor apparatus according to claim 11 wherein said support elements each comprise set screws at each end thereof for removable securement to the opposing sides of said base.

13. A retractor apparatus according to claim 11 including a plurality of sutures each having a first end for being attached to a suture button and a second end for being secured to one of said suture anchor elements.

14. A retractor apparatus according to claim 13 wherein said suture buttons are formed from material selected from the group consisting of radiopaque or translucent polymer.

15. A retractor apparatus according to claim 11 wherein said base and said support elements are constructed of stainless steel.

16. A retractor apparatus according to claim 11 wherein said base is formed of stainless steel and said support elements are formed of translucent polymer.

17. A retractor apparatus according to claim 11 comprising a plurality of said frames being detachably secured together to form an extended-length retractor apparatus.

18. A retractor apparatus according to claim 17 wherein said plurality of frames consists of three frames.

19. A method of balloon dissection of internal body tissue of a human body part using an external retractor apparatus for maintaining an open cavity within the dissected internal body tissue during a surgical procedure, comprising the steps of:

(a) providing a human body part upon which balloon dissection will be performed during a surgical procedure;

(b) positioning the body part within an external retractor apparatus comprising a base with opposing sides and at least one arcuate body tissue support element extending upwardly from one side to the other side of said base so as to extend transversely over and in spaced-apart relationship to the body part; and (c) pulling at least one suture from within the dissected body tissue cavity and outwardly of the human body part so that one end remains trapped therein and then securing the other end under tension to a corresponding suture anchor element located at a location along the length of said support element;

whereby the dissected internal body tissue of the human body part is maintained by the external retractor apparatus in an open cavity relationship to facilitate the surgical procedure.

20. A method according to claim 19 including providing a retractor apparatus comprising a plurality of arcuate body tissue support elements having a plurality of suture anchor elements selectively located thereon and pulling a plurality of sutures from within the dissected body tissue cavity and securing the sutures under tension to said suture anchor elements.

21. A method according to claim 19 including performing a surgical procedure within the open cavity subsequent to securing of the suture to said suture anchor element of said external retractor apparatus.

22. A method of balloon dissection of internal body tissue of a human body part using an external retractor apparatus for maintaining an open cavity within the dissected internal body tissue during a surgical procedure, comprising the steps of:

(a) providing a human body part upon which balloon dissection will be performed during a surgical procedure;

(b) positioning the body part within an external retractor apparatus comprising a base with opposing sides and a plurality of arcuate body tissue support elements extending upwardly from one side to the other side of said base so as to extend transversely over and in spaced-apart relationship to the body part; and (c) pulling a plurality of sutures from within the dissected body tissue cavity and outwardly of the human body part so that one end of each remains trapped therein and then securing the other end of each suture under tension to one of a plurality of corresponding suture anchor elements located on said support elements;

whereby the dissected internal body tissue of the human body part is maintained by the external retractor apparatus in an open cavity relationship to facilitate the surgical procedure.

23. A method according to claim 22 including performing a surgical procedure within the open cavity subsequent to securing of the sutures to said suture anchor elements of said external retractor apparatus.

24. A method according to claim 23 wherein the surgical procedure comprises the removal of a portion of the length of a saphenous vein from a leg of a human during cardiac by-pass surgery.

* * * * *